(12) United States Patent
Li et al.

(10) Patent No.: US 11,538,588 B2
(45) Date of Patent: Dec. 27, 2022

(54) ATRIAL FIBRILLATION SIGNAL RECOGNITION METHOD, APPARATUS AND DEVICE

(71) Applicant: SHENZHEN INSTITUTES OF ADVANCED TECHNOLOGY CHINESE ACADEMY OF SCIENCES, Shenzhen (CN)

(72) Inventors: Ye Li, Shenzhen (CN); Xiaomao Fan, Shenzhen (CN); Qihang Yao, Shenzhen (CN); Liyan Yin, Shenzhen (CN)

(73) Assignee: SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 289 days.

(21) Appl. No.: 16/901,033

(22) Filed: Jun. 15, 2020

(65) Prior Publication Data
US 2020/0312459 A1    Oct. 1, 2020

Related U.S. Application Data

(63) Continuation of application No. PCT/CN2017/120106, filed on Dec. 29, 2017.

(30) Foreign Application Priority Data

Dec. 19, 2017   (CN) .......................... 201711380466.9

(51) Int. Cl.
*G06N 3/00*      (2006.01)
*G16H 50/20*     (2018.01)
(Continued)

(52) U.S. Cl.
CPC ............ *G16H 50/20* (2018.01); *A61B 5/352* (2021.01); *A61B 5/361* (2021.01); *A61B 5/7267* (2013.01); *G06N 3/0454* (2013.01); *G06N 3/08* (2013.01)

(58) Field of Classification Search
CPC ........ G16H 50/20; A61B 5/352; A61B 5/361; A61B 5/7267; A61B 5/7264; A61B 5/318; G06N 3/0454; G06N 3/08
(Continued)

(56) References Cited

U.S. PATENT DOCUMENTS

2014/0257122 A1*  9/2014  Ong ....................... A61B 5/316
                                                              705/2
2017/0032221 A1*  2/2017  Wu .......................... A61B 7/04

FOREIGN PATENT DOCUMENTS

CN      104970789 A      10/2015
CN      105726018 A  *    7/2016
(Continued)

OTHER PUBLICATIONS

C. Bruser, J. Diesel, M. D. H. Zink, S. Winter, P. Schauerte and S. Leonhardt, "Automatic Detection of Atrial Fibrillation in Cardiac Vibration Signals," in IEEE Journal of Biomedical and Health Informatics, vol. 17, No. 1, pp. 162-171, Jan. 2013, doi: 10.1109/TITB.2012.2225067. (Year: 2013).*

(Continued)

*Primary Examiner* — Van D Huynh (57) ABSTRACT

The present disclosure provides an atrial fibrillation signal recognition method, apparatus and device. The method comprises: obtaining an electrocardiogram signal to be recognized; inputting the electrocardiogram signal to be recognized to a pre-established atrial fibrillation signal recognition model, and outputting an atrial fibrillation signal recognition result, where the atrial fibrillation signal recognition model is established in the following way: obtaining (Continued)

a specified number of electrocardiogram sample signals and corresponding identifier information; balancing, according to the number of normal signals, atrial fibrillation signals by means of SMOTE; establishing a network structure of multiple convolutional neural networks, each of the convolutional neural networks being provided with a specific receptive field for recognizing the atrial fibrillation signals of a corresponding granularity; and inputting the normal signals and the balanced atrial fibrillation signals to the network structure for training to generate an atrial fibrillation signal recognition model.

9 Claims, 4 Drawing Sheets

(51) Int. Cl.
*A61B 5/00* (2006.01)
*G06N 3/04* (2006.01)
*G06N 3/08* (2006.01)
*A61B 5/352* (2021.01)
*A61B 5/361* (2021.01)

(58) Field of Classification Search
USPC .......................................................... 706/20
See application file for complete search history.

(56) References Cited

FOREIGN PATENT DOCUMENTS

| | | |
|---|---|---|
| CN | 105726018 A | 7/2016 |
| CN | 107391900 A | 11/2017 |

OTHER PUBLICATIONS

International Search Report issued in corresponding International application No. PCT/CN2017/120106, dated Aug. 23, 2018(8 pages).
First Office Action from China patent office in a counterpart Chinese patent Application 201711380466.9, dated Dec. 18, 2018 (9 pages).
Decision to grant patent from China patent office in a counterpart Chinese patent Application 201711380466.9, dated May 23, 2019 (1 page).
Written Opinion of the International Searching Authority for No. PCT/CN2017/120106.
IEEE Journal of Biomedical and Health Informatics, vol. 17, No. 1, Jan. 2013 (10 pages).

* cited by examiner

ATRIAL FIBRILLATION SIGNAL RECOGNITION METHOD, APPARATUS AND DEVICE

CROSS-REFERENCE TO RELATED APPLICATIONS

This application is a continuation application of International Application No. PCT/CN2017/120106, filed on Dec. 29, 2017, which claims priority to Chinese Patent Application No. 201711380466.9, filed on Dec. 19, 2017. The disclosures of the aforementioned patent applications are hereby incorporated by reference in their entireties.

TECHNICAL FIELD

The present disclosure relates to the field of electrocardiogram monitoring technologies, and in particular, to an atrial fibrillation signal recognition method, apparatus and device.

BACKGROUND

Atrial fibrillation is the most common persistent chronic arrhythmia, which usually results from a disordered atrial activity and irregular atrial contraction. An atrial fibrillation signal in an electrocardiogram signal can be recognized by detecting variability of a P wave or an RR interval. However, recognition reliability and accuracy of these methods are insufficient to meet the needs of clinical diagnosis. Consequently, these methods are not widely used in medical diagnosis or wearable monitoring devices.

With the rapid development of artificial intelligence, a method for recognizing an atrial fibrillation signal through machine learning emerges. However, this recognition method requires a long electrocardiogram signal and has high requirements for data processing. This method generally requires manual extraction of signal characteristics and noise reduction processing. For dynamic electrocardiogram signals collected by a wearable single-lead device, recognition reliability and accuracy of this method are still insufficient to meet the needs of clinical diagnosis.

SUMMARY

In view of the above, an objective of the present disclosure is to provide an atrial fibrillation signal recognition method, apparatus and device, so as to improve the reliability and accuracy of atrial fibrillation signal recognition.

To achieve the foregoing objective, the present disclosure uses the following technical solutions:

According to a first aspect, the present disclosure provides an atrial fibrillation signal recognition method. The method includes: obtaining an electrocardiogram signal to be recognized; inputting the electrocardiogram signal to be recognized to a pre-established atrial fibrillation signal recognition model, and outputting an atrial fibrillation signal recognition result, where the atrial fibrillation signal recognition model is established in the following way: obtaining a specified number of electrocardiogram sample signals and corresponding identifier information, where the identifier information includes identifier information of normal signals and of atrial fibrillation signals; balancing, according to the number of normal signals, atrial fibrillation signals by means of synthetic minority oversampling technique (SMOTE); establishing a network structure of multiple convolutional neural networks, each of the convolutional neural networks being provided with a specific receptive field for recognizing the atrial fibrillation signals of a corresponding granularity; and inputting the normal signals and the balanced atrial fibrillation signals to the network structure for training to generate an atrial fibrillation signal recognition model.

According to a second aspect, the present disclosure provides an atrial fibrillation signal recognition apparatus. The apparatus includes: a signal obtaining module, configured to obtain an electrocardiogram signal to be recognized; and a result outputting module, configured to input the electrocardiogram signal to be recognized to a pre-established atrial fibrillation signal recognition model, and output an atrial fibrillation signal recognition result, where the atrial fibrillation signal recognition model is established in the following way: obtaining a specified number of electrocardiogram sample signals and corresponding identifier information, where the identifier information includes identifier information of normal signals and of atrial fibrillation signals; balancing, according to the number of normal signals, atrial fibrillation signals by means of SMOTE; establishing a network structure of multiple convolutional neural networks, each of the convolutional neural networks being provided with a specific receptive field for recognizing the atrial fibrillation signals of a corresponding granularity; and inputting the normal signals and the balanced atrial fibrillation signals to the network structure for training to generate an atrial fibrillation signal recognition model.

According to a third aspect, the present disclosure provides an atrial fibrillation signal recognition device, including a processor and a machine-readable storage medium, where the machine-readable storage medium stores a machine-executable instruction that can be executed by the processor, and the processor executes the machine-executable instruction to perform the foregoing atrial fibrillation signal recognition method.

According to a fourth aspect, the present disclosure provides a machine-readable storage medium, where the machine-readable storage medium stores a machine-executable instruction; and when being invoked and executed by a processor, the machine-executable instruction enables the processor to perform the foregoing atrial fibrillation signal recognition method.

According to the foregoing atrial fibrillation signal recognition method, apparatus and device, and the machine-readable storage medium, the atrial fibrillation signal recognition model is established through training on multiple convolutional neural networks, and each of the convolutional neural networks is provided with a specific receptive field for recognizing the atrial fibrillation signals of a corresponding granularity; the atrial fibrillation signal recognition result can be obtained by inputting the electrocardiogram signal to be recognized to the atrial fibrillation signal recognition model. In this method, multiple convolutional neural networks with different sizes of receptive fields are used to recognize atrial fibrillation signals, so that atrial fibrillation signals of different granularities can be recognized. This can comprehensively recognize atrial fibrillation signals, thereby improving the reliability and accuracy of atrial fibrillation signal recognition.

In addition, this method requires short duration of the electrocardiogram signal, and no manual intervention is required in the recognition process, so that atrial fibrillation signals can be automatically and efficiently recognized.

Other features and advantages of the present disclosure will be described in the subsequent specification, or some features and advantages can be inferred or unambiguously determined from the specification, or can be known by implementing the foregoing technologies of the present disclosure.

To make the foregoing objectives, features, and advantages of the present disclosure clearer and more comprehensible, the following provides a detailed description by using preferred embodiments with reference to the accompanying drawings.

BRIEF DESCRIPTION OF DRAWINGS

To describe the technical solutions in the embodiments of the present disclosure or in the existing technology more clearly, the following briefly describes the accompanying drawings needed for describing the embodiments or the existing technology. Clearly, the accompanying drawings in the following description show some embodiments of the present disclosure, and a person of ordinary skill in the art can still derive other drawings from these accompanying drawings without creative efforts.

DESCRIPTION OF EMBODIMENTS

To make the objectives, technical solutions, and advantages of the embodiments of the present disclosure clearer, the following clearly and comprehensively describes the technical solutions in the present disclosure with reference to the accompanying drawings. Clearly, the described embodiments are some but not all of the embodiments of the present disclosure. All other embodiments obtained by a person of ordinary skill in the art based on the embodiments of the present disclosure without creative efforts shall fall within the protection scope of the present disclosure.

Atrial fibrillation is the most common persistent chronic arrhythmia, which usually results from a disordered atrial activity and irregular atrial contraction. Atrial fibrillation is closely related to a variety of diseases such as stroke, heart failure, coronary heart disease and thrombosis. Early recognition of atrial fibrillation can help patients detect cardiac abnormalities in time and reduce the disability rate and fatality rate caused by a heart disease.

An atrial fibrillation signal in an electrocardiogram (ECG) signal can be recognized by detecting variability of a P wave or an RR interval. For example, an atrial fibrillation signal is recognized based on P-wave trigger signal equalization; an atrial fibrillation signal in hypertensive population is recognized according to the principle of P-wave disappearance; and an atrial fibrillation signal is recognized based on an RR interval of randomness, variability and complexity. However, recognition reliability and accuracy of these methods are insufficient to meet the needs of clinical diagnosis. Consequently, these methods are not widely used in medical diagnosis or wearable monitoring devices.

With the rapid development of artificial intelligence, a method for recognizing an atrial fibrillation signal through machine learning emerges in the existing technology. For example, a single-channel and single-lead atrial fibrillation signal is recognized by using an extended nonlinear Bayesian network. However, this recognition method requires a long electrocardiogram signal (generally more than 30 seconds) and has high requirements for data processing. This method generally requires manual extraction of signal characteristics and noise reduction processing. For dynamic electrocardiogram signals collected by a wearable single-lead device, recognition reliability and accuracy of this method are still insufficient to meet the needs of clinical diagnosis.

To resolve the foregoing problem of low accuracy of atrial fibrillation signal recognition, the embodiments of the present disclosure provide an atrial fibrillation signal recognition method, apparatus and device. The technology can be applied to a server, and may be further applied to terminal devices such as a wearable heart monitoring device, a mobile phone, a tablet computer, etc. The technology is used to recognize an atrial fibrillation signal and assist in diagnosing persistent chronic arrhythmia and other heart diseases. This technology can be implemented using relevant software or hardware, and will be described with embodiments in the following.

Figure 1:
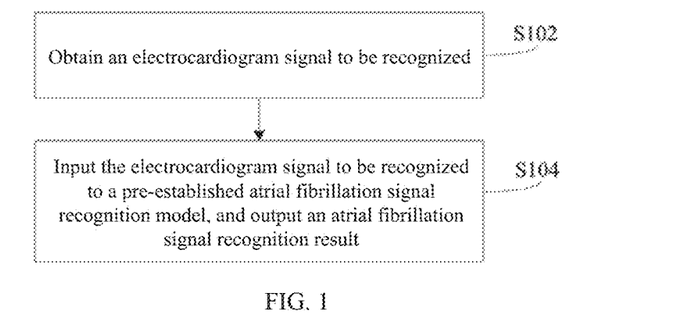
FIG. 1 is a flowchart of an atrial fibrillation signal recognition method according to an embodiment of the present disclosure.

FIG. 1 is a flowchart of an atrial fibrillation signal recognition method. The method includes the following steps:

Step S102: Obtain an electrocardiogram signal to be recognized.

Step S104: Input the electrocardiogram signal to be recognized to a pre-established atrial fibrillation signal recognition model, and output an atrial fibrillation signal recognition result.

The electrocardiogram signal to be recognized generally includes a normal signal and an atrial fibrillation signal. The electrocardiogram signal to be recognized may be an original electrocardiogram signal collected by a device. To improve accuracy of a recognition result, the original electrocardiogram signal can be preprocessed before the recognition, for example, filtering, noise reduction, rectified linear units (RELU) activation function processing, and regularization processing. The preprocessed electrocardiogram signal can better adapt to an atrial fibrillation signal recognition model and improve the recognition effect.

Figure 2:
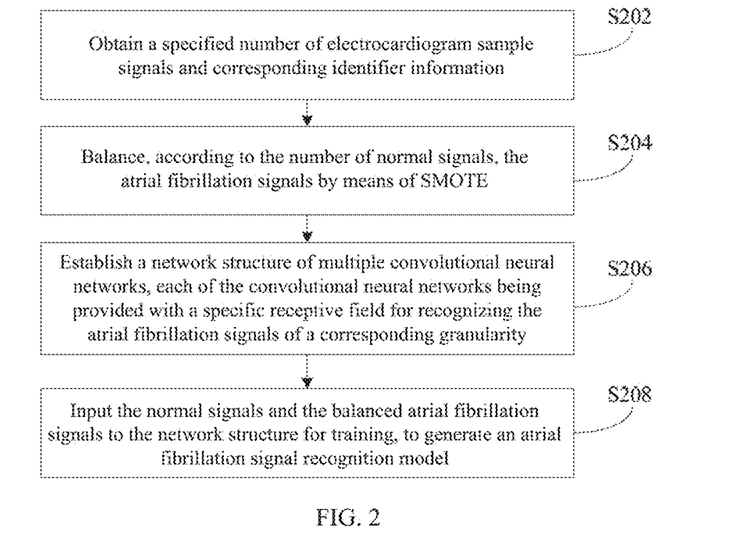
FIG. 2 is a specific flowchart of establishing an atrial fibrillation signal recognition model according to an embodiment of the present disclosure.

FIG. 2 is a specific flowchart of establishing an atrial fibrillation signal recognition model. The atrial fibrillation signal recognition model is established in the following way:

Step S202: Obtain a specified number of electrocardiogram sample signals and corresponding identifier information, where the identifier information includes identifier information of normal signals and of atrial fibrillation signals.

Step S204: Balance, according to the number of normal signals, the atrial fibrillation signals by means of synthetic minority oversampling technique (SMOTE).

Step S206: Establish a network structure of multiple convolutional neural networks, each of the convolutional neural networks being provided with a specific receptive field for recognizing the atrial fibrillation signals of a corresponding granularity.

A segment of electrocardiogram signals generally includes only a few atrial fibrillation signals, and the number of normal signals is much larger than the number of atrial fibrillation signals. The numbers of the two types of signals are unbalanced. If such data is used to train the network structure of the neural network, the recognition effect of the model may be affected. Based on this, SMOTE is used to balance the atrial fibrillation signal in step S204. SMOTE can be used to analyze minority class samples, and manually synthesize new samples based on the minority class samples and add the new samples to a data set. Therefore, SMOTE can be used to increase the number of atrial fibrillation signals, so that the atrial fibrillation signals are roughly balanced with the normal signals, facilitating the training of the network structure.

Step S208: Input the normal signals and the balanced atrial fibrillation signals to the network structure for training to generate the atrial fibrillation signal recognition model.

It can be learned from the foregoing description that, the atrial fibrillation signal originates from a disordered atrial activity and irregular atrial contraction. Therefore, the atrial fibrillation signal has multiple forms. For example, some atrial fibrillation signals have a large granularity, a significant waveform or a high wave height; and some other atrial fibrillation signals have a small granularity, a weak waveform or a low wave height. Due to a single receptive field, a single-channel convolutional neural network usually can only perceive an atrial fibrillation signal within a narrow granularity range, and hardly learn and recognize various forms of atrial fibrillation signals, resulting in incomplete recognition and low recognition accuracy.

Based on this, in this embodiment, multiple convolutional neural networks are used to establish the atrial fibrillation signal recognition model, and each convolutional neural network is provided with a specific receptive field for recognizing the atrial fibrillation signals of a corresponding granularity. A convolutional neural network with a smaller receptive field can recognize atrial fibrillation signals with a smaller granularity, and a convolutional neural network with a larger receptive field can recognize atrial fibrillation signals with a larger granularity.

Each neural network is constructed by multiple convolutional layers, and a receptive field of a convolution kernel of each convolutional layer can be set separately. Therefore, the receptive fields of the convolution kernels of the convolutional layers in each neural network may be the same or different. When the receptive fields of the convolution kernels of the convolutional layers are different, the receptive fields of the convolution kernels of the convolutional layers can increase or decrease on a layer-by-layer basis, or can be set in other ways. In addition, the above-mentioned convolutional neural network may be a multi-scale convolutional neural network (MS-CNN), or may be another type of neural network.

According to the atrial fibrillation signal recognition method provided in this embodiment of the present disclosure, the atrial fibrillation signal recognition model is established through training on multiple convolutional neural networks, and each of the convolutional neural networks is provided with a specific receptive field for recognizing the atrial fibrillation signals of a corresponding granularity; the atrial fibrillation signal recognition result can be obtained by inputting the electrocardiogram signal to be recognized to the atrial fibrillation signal recognition model. In this method, multiple convolutional neural networks with different sizes of receptive fields are used to recognize atrial fibrillation signals, so that atrial fibrillation signals of different granularities can be recognized. This can comprehensively recognize atrial fibrillation signals, thereby improving the reliability and accuracy of atrial fibrillation signal recognition.

In addition, this method requires short duration of the electrocardiogram signal, and no manual intervention is required in the recognition process, so that atrial fibrillation signals can be automatically and efficiently recognized.

Figure 3:
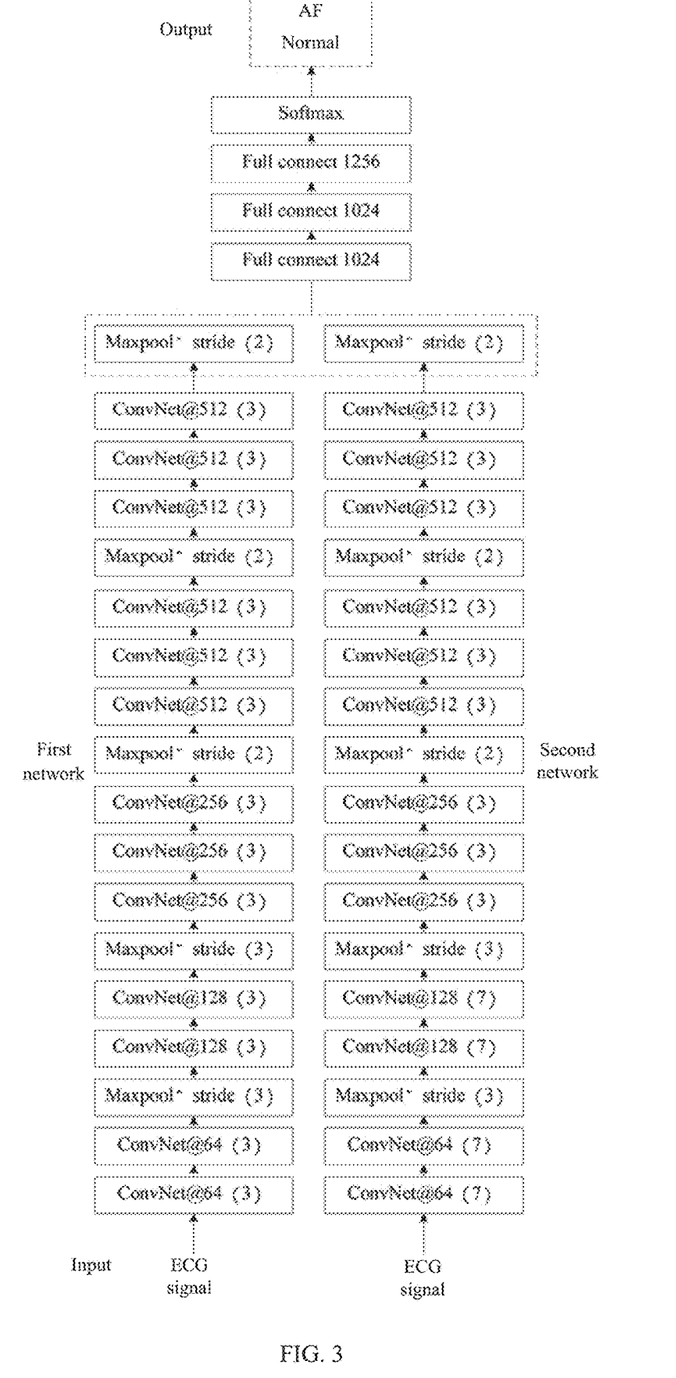
FIG. 3 is a schematic structural diagram of an atrial fibrillation signal recognition model according to an embodiment of the present disclosure.

FIG. 3 is a schematic structural diagram of an atrial fibrillation signal recognition model. For example, the network structure of multiple convolutional neural networks in FIG. 3 includes two neural networks: a first network and a second network, In this embodiment, both the first network and the second network are VGG-16 convolutional neural networks. Certainly, the first network and the second network may also be other types of convolutional neural networks such as CaffeNet and ResNet.

Each of the first network and the second network includes multiple convolutional layers and multiple max-pooling layers. As shown in FIG. 3, the first network includes 13 convolutional layers (i.e., ConvNet layers in FIGS. 3) and 5 max-pooling layers (i.e., Maxpool layers in FIG. 3). The 13 convolutional layers are arranged in sequence, and the 5 max-pooling layers are interposed among the 13 convolutional layers. The second network also includes 13 convolutional layers and 5 max-pooling layers. The 13 convolutional layers are arranged in sequence, and the 5 max-pooling layers are interposed among the 13 convolutional layers.

To recognize atrial fibrillation signals of different granularities, the receptive field of the convolution kernel in the first network can be set to be less than or equal to the receptive field of the convolution kernel in the second network. As shown in FIG. 3, the receptive fields of the convolution kernels of the 13 convolutional layers in the first network are the same, that is, are all 3. Certainly, the receptive field can also be changed to another value. The receptive fields of the convolution kernels of the 13 convolutional layers in the second network may be set to different values. For example, in FIG. 3, from left to right, the receptive fields of the convolution kernels of the first four convolutional layers are all set to 7, and the receptive fields of the convolution kernels of the other convolutional layers are all set to 3. Certainly, the receptive fields of the convolution kernels of the first four convolutional layers may also be set to 3, 5, 9, or the like, and the receptive fields of the convolution kernels of the other convolutional layers except for the first four convolutional layers may also be flexibly set to other values.

Table 1 shows multiple parameter configurations for the atrial fibrillation signal recognition model. In the MS-CNN (3, 3) configuration, the receptive fields of the convolution kernels of the convolutional layers in the first network are all 3; the receptive fields of the convolution kernels of the convolutional layers in the second network are all 3. In the MS-CNN (3, 5) configuration, the receptive fields of the convolution kernels of the convolutional layers in the first network are all 3; the receptive fields of the convolution kernels of the first four convolutional layers in the second network are 5, and the receptive fields of the convolution kernels of other layers are 3. In the MS-CNN (3, 7) configuration, the receptive fields of the convolution kernels of the convolutional layers in the first network are all 3; the receptive fields of the convolution kernels of the first four convolutional layers in the second network are 7. and the receptive fields of the convolution kernels of other layers are 3. In the MS-CNN (3, 9) configuration, the receptive fields of the convolution kernels of the convolutional layers in the first network are all 3; the receptive fields of the convolution kernels of the first four convolutional layers in the second network are 9, and the receptive fields of the convolution kernels of other layers are 3.

TABLE 1

| MS-CNN (3, 3) | | MS-CNN (3, 5) | | MS-CNN (3, 7) | | MS-CNN (3, 9) | |
|---|---|---|---|---|---|---|---|
| Stream 1 | Stream2 | Stream 1 | Stream2 | Stream 1 | Stream2 | Stream 1 | Stream2 |
| Input | | | | | | | |
| Conv (3)-64 | Conv (3)-64 | Conv (3)-64 | Conv (5)-64 | Conv (3)-64 | Conv (7)-64 | Conv (3)-64 | Conv (9)-64 |
| Conv (3)-64 | Conv (3)-64 | Conv (3)-64 | Conv (5)-64 | Conv (3)-64 | Conv (7)-64 | Conv (3)-64 | Conv (9)-64 |
| Maxpool, stride (3) | | | | | | | |
| Conv (3)-128 | Conv (3)-128 | Conv (3)-128 | Conv (5)-128 | Conv (3)-128 | Conv (7)-128 | Conv (3)-128 | Conv (9)-128 |
| Conv (3)-128 | Conv (3)-128 | Conv (3)-128 | Conv (5)-128 | Conv (3)-128 | Conv (7)-128 | Conv (3)-128 | Conv (9)-128 |
| Maxpool, stride (3) | | | | | | | |
| Conv (3)-256 | Conv (3)-256 | Conv (3)-256 | Conv (3)-256 | Conv (3)-256 | Conv (3)-256 | Conv (3)-256 | Conv (3)-256 |
| Conv (3)-256 | Conv (3)-256 | Conv (3)-256 | Conv (3)-256 | Conv (3)-256 | Conv (3)-256 | Conv (3)-256 | Conv (3)-256 |
| Conv (3)-256 | Conv (3)-256 | Conv (3)-256 | Conv (3)-256 | Conv (3)-256 | Conv (3)-256 | Conv (3)-256 | Conv (3)-256 |
| Maxpool, stride (2) | | | | | | | |
| Conv (3)-512 | Conv (3)-512 | Conv (3)-512 | Conv (3)-512 | Conv (3)-512 | Conv (3)-512 | Conv (3)-512 | Conv (3)-512 |
| Conv (3)-512 | Conv (3)-512 | Conv (3)-512 | Conv (3)-512 | Conv (3)-512 | Conv (3)-512 | Conv (3)-512 | Conv (3)-512 |
| Conv (3)-512 | Conv (3)-512 | Conv (3)-512 | Conv (3)-512 | Conv (3)-512 | Conv (3)-512 | Conv (3)-512 | Conv (3)-512 |
| Maxpool, stride (2) | | | | | | | |
| Conv (3)-512 | Conv (3)-512 | Conv (3)-512 | Conv (3)-512 | Conv (3)-512 | Conv (3)-512 | Conv (3)-512 | Conv (3)-512 |
| Conv (3)-512 | Conv (3)-512 | Conv (3)-512 | Conv (3)-512 | Conv (3)-512 | Conv (3)-512 | Conv (3)-512 | Conv (3)-512 |
| Conv (3)-512 | Conv (3)-512 | Conv (3)-512 | Conv (3)-512 | Conv (3)-512 | Conv (3)-512 | Conv (3)-512 | Conv (3)-512 |
| Maxpool, stride (2) | | | | | | | |
| Concatenation | | | | | | | |
| Full-connection-1024 | | Full-connection-1024 | | Full-connection-1024 | | Full-connection-1024 | |
| Full-connection-1024 | | Full-connection-1024 | | Full-connection-1024 | | Full-connection-1024 | |
| Full-connection-256 | | Full-connection-256 | | Full-connection-256 | | Full-connection-2 5 6 | |
| Softmax | | Softmax | | Softmax | | Softmax | |

In this atrial fibrillation signal recognition model, the max-pooling layers of the last layers of the first network and the second network are connected to each other, The interconnected max-pooling layers are further successively connected to multiple fully connected layers (i.e., the Full connect layers in FIG. 3) and a Softmax layer. As shown in FIG. 3, the max-pooling layers of the last layers of the first network and the second network are connected in parallel, and are further successively connected to four fully connected layers and one Softmax layer.

When this atrial fibrillation signal recognition model is used for recognition, the electrocardiogram (ECG) signal (equivalent to the above-mentioned electrocardiogram signal) is separately input to the first convolutional layers of the first network and the second network, and then is processed by various convolutional layers, max-pooling layers, and fully connected layers. Then the Softmax layer outputs a classification result, and the result includes atrial fibrillation signals AF and normal signals Normal. Further, atrial fibrillation signals are recognized.

During the establishment of the atrial fibrillation signal recognition model, the inventor usually needs to repeatedly adjust various configuration parameters to maximize the recognition effect of the model. Based on this, during the establishment of the atrial fibrillation signal recognition model, the step of inputting the normal signals and the balanced atrial fibrillation signals to the network structure for training to generate an atrial fibrillation signal recognition model specifically includes the following:

Step 1: Input the normal signals and the balanced atrial fibrillation signals to the network structure for training to generate an initial model.

Step 2: Calculate sensitivity of the atrial fibrillation signal recognition model:

$$Sen = \frac{\#(TP)}{\#(TP) + \#(FN)}.$$

Step 3: Calculate specificity of the atrial fibrillation signal recognition model:

$$Spe = \frac{\#(TN)}{\#(TN) + \#(FP)}.$$

Step 4: Calculate precision of the atrial fibrillation signal recognition model:

$$Pre = \frac{\#(TP)}{\#(TP) + \#(FP)}.$$

Step 5: Calculate accuracy of the atrial fibrillation signal recognition model:

$$Acc = \frac{\#(TP) + \#(TN)}{\#(TP + TN + FN + FP)}.$$

In the foregoing steps, # represents the number; TP represents a correctly recognized atrial fibrillation signal; FP represents an incorrectly recognized atrial fibrillation signal; TN represents a correctly recognized normal signal; FN represents an incorrectly recognized normal signal.

Step 6: Determine whether the sensitivity, the specificity, the precision, and the accuracy meet corresponding thresholds respectively. If no, adjust configuration parameters in the network structure until the sensitivity, the specificity, the precision, and the accuracy meet the corresponding thresholds.

Figure 4:
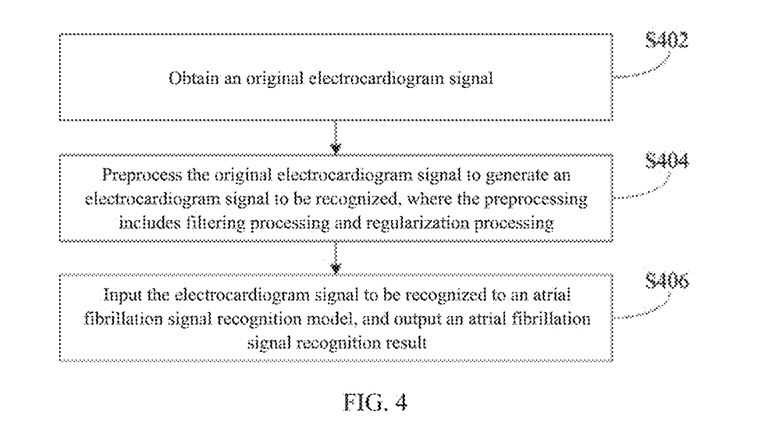
FIG. 4 is a flowchart of another atrial fibrillation signal recognition method according to an embodiment of the present disclosure.

Step 7: Determine the initial model as the atrial fibrillation signal recognition model, FIG. 4 is a flowchart of another atrial fibrillation signal recognition method. The method is implemented by using the atrial fibrillation signal recognition model shown in FIG. 3, The method includes the following steps:

Step S402: Obtain an original electrocardiogram signal.

Step S404: Preprocess the original electrocardiogram signal to generate an electrocardiogram signal to be recognized, where the preprocessing includes filtering processing and regularization processing.

A frequency width of an electrocardiogram signal collected by an electrocardiogram collector or another heart detection device is large and exceeds 150 Hz. The inventor has found, through repeated tests, that frequencies that greatly contribute to the recognition of the atrial fibrillation signal are mostly between 0.5 Hz and 40 Hz. Therefore, to reduce an interfering signal during model recognition and reduce an amount of data, and improve recognition efficiency, the electrocardiogram signal needs to be filtered before being input to the model. For example, a finite impulse response (FIR) filter can be used to downsample the original electrocardiogram signal to filter out high-frequency noise. The parameters of the FIR filter can be set as a 512th order low-pass filter with a cut-off frequency of 60 Hz, and then the original electrocardiogram signal can be downsampled to 120 Hz.

Generally, before recognition processing, the atrial fibrillation signal recognition model needs to be activated by using an activation function. The model in this embodiment is established by using two convolutional neural networks, and the RELU algorithm is not suitable for the model that is established by using two convolutional neural networks. Therefore, in this embodiment, regularization processing is performed to prevent fitting of the model, which is beneficial to diversity of gradient descending of model nodes.

Step S406: Input the electrocardiogram signal to be recognized to the atrial fibrillation signal recognition model, and output an atrial fibrillation signal recognition result.

According to the atrial fibrillation signal recognition method provided in this embodiment of the present disclosure, the atrial fibrillation signal recognition model is established through training on two convolutional neural networks, and each of the convolutional neural networks is provided with a specific receptive field for recognizing the atrial fibrillation signals of a corresponding granularity; the atrial fibrillation signal recognition result can be obtained by performing filtering processing and regularization processing on the electrocardiogram signal and then inputting the processed electrocardiogram signal to the atrial fibrillation signal recognition model. In this method, multiple convolutional neural networks with different sizes of receptive fields are used to recognize atrial fibrillation signals, so that atrial fibrillation signals of different granularities can be recognized. This can comprehensively recognize atrial fibrillation signals, thereby improving the reliability and accuracy of atrial fibrillation signal recognition.

In addition, this method requires short duration of the electrocardiogram signal, and no manual intervention is required in the recognition process, so that atrial fibrillation signals can be automatically and efficiently recognized.

Figure 5:
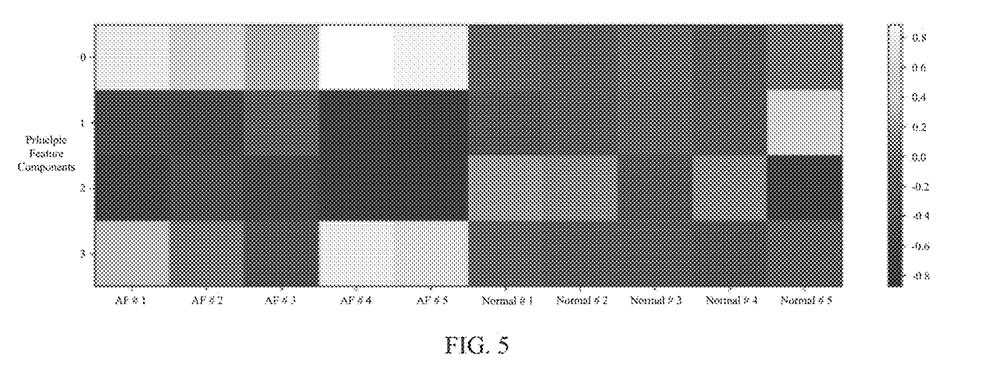
FIG. 5 is a thermodynamic diagram of an atrial fibrillation signal recognition result according to an embodiment of the present disclosure.

To verify the recognition effect of the atrial fibrillation signal recognition method, the inventor has further analyzed the data that is output by the atrial fibrillation signal recognition model. FIG. 5 is a thermodynamic diagram of an atrial fibrillation signal recognition result. In the atrial fibrillation signal recognition model, the 256-dimensional feature data that is output by the Softmax layer is subjected to principal component analysis, and four pieces of principal component data are intercepted for display. FIG. 5 is a thermodynamic diagram of four pieces of principal component data for five atrial fibrillation signals and five normal signals. It can be seen from the figure that the gray values of the atrial fibrillation signals AF and the normal signals Normal have significantly different characteristics, and the difference is obvious, indicating that the recognition effect of the atrial fibrillation signal recognition method is good.

Table 2 shows the accuracy of atrial fibrillation signal recognition in each configuration of the receptive field. Table 2 provides statistical data of the sensitivity Sen, specificity Spe, precision Pre, and accuracy Acc corresponding to four input lengths of the electrocardiogram signal under four parameter configurations (MS-CNN (3, 3), MS-CNN (3, 5), MS-CNN (3, 7), and MS-CNN (3, 9)), Table 2 shows that the model has accuracy of not less than 96% for the data input lengths of 5 seconds, 10 seconds, 20 seconds, and 30 seconds. Under the MS-CNN (3, 7) configuration, the accuracy corresponding to the input length of 20 seconds reaches 98.13%.

TABLE 2

| Model | Input length | Sen | Spe | Pre | Acc |
| --- | --- | --- | --- | --- | --- |
| MS-CNN(3, 3) | 5 s | 91.6% | 97.52% | 84.39% | 96.77% |
| | 10 s | 93.09% | 98.28% | 88.76% | 97.62% |
| | 20 s | 94.31% | 98.69% | 91.35% | 98.13% |
| | 30 s | 85.91% | 98.91% | 92.02% | 97.25% |
| MS-CNN(3, 5) | 5 s | 92.41% | 97.70% | 85.43% | 96.99% |
| | 10 s | 93.36% | 98.24% | 88.56% | 97.62% |
| | 20 s | 93.77% | 98.71% | 91.41% | 98.08% |
| | 30 s | 89.16% | 97.54% | 84.14% | 96.48% |
| MS-CNN(3, 7) | 5 s | 92.28% | 97.60% | 84.91% | 96.92% |
| | 10 s | 93.63% | 98.14% | 88.03% | 97.56% |
| | 20 s | 93.77% | 98.77% | 91.78% | 98.13% |
| | 30 s | 85.91% | 98.91% | 92.02% | 97.25% |
| MS-CNN(3, 9) | 5 s | 92.41% | 97.62% | 85.04% | 96.96% |
| | 10 s | 93.63% | 98.34% | 89.16% | 97.14% |
| | 20 s | 92.68% | 98.61% | 90.72% | 97.86% |
| | 30 s | 88.62% | 98.73% | 91.09% | 97.44% |

Figure 6:
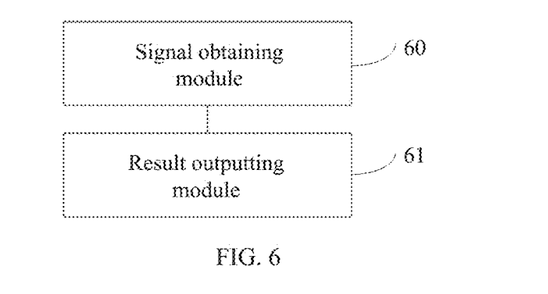
FIG. 6 is a schematic structural diagram of an atrial fibrillation signal recognition apparatus according to an embodiment of the present disclosure.

Corresponding to the foregoing method embodiment, FIG. 6 is a schematic structural diagram of an atrial fibrillation signal recognition apparatus. The apparatus includes:

a signal obtaining module 60, configured to obtain an electrocardiogram signal to be recognized; and a result outputting module 61, configured to input the electrocardiogram signal to be recognized to a pre-established atrial fibrillation signal recognition model, and output an atrial fibrillation signal recognition result, where the atrial fibrillation signal recognition model is established in the following way: obtaining a specified number of electrocardiogram sample signals and corresponding identifier information, where the identifier information includes identifier information of normal signals and of atrial fibrillation signals; balancing, according to the number of normal signals, atrial fibrillation signals by means of SMOTE; establishing a network structure of multiple convolutional neural networks, each of the convolutional neural networks being provided with a specific receptive field for recognizing the atrial fibrillation signals of a corresponding granularity; and inputting the normal signals and the balanced atrial fibrillation signals to the network structure for training to generate an atrial fibrillation signal recognition model.

The network structure of the multiple convolutional neural networks includes a first network and a second network. Both the first network and the second network are VGG-16 convolutional neural networks. Each of the first network and the second network includes multiple convolutional layers and multiple max-pooling layers. The receptive field of the convolution kernel in the first network is less than or equal to the receptive field of the convolution kernel in the second network. The max-pooling layers of the last layers of the first network and the second network are connected to each other. The interconnected max-pooling layers are further successively connected to multiple fully connected layers and a Softmax layer.

The signal obtaining module is further configured to obtain an original electrocardiogram signal; and preprocess the original electrocardiogram signal to generate an electrocardiogram signal to be recognized, where the preprocessing includes filtering processing and regularization processing.

The result outputting module is further configured to input the normal signals and the balanced atrial fibrillation signals to the network structure for training to generate an initial model;

calculate sensitivity of the initial model:

$$Sen = \frac{\#(TP)}{\#(TP) + \#(FN)};$$

calculate specificity of the initial model:

$$Spe = \frac{\#(TN)}{\#(TN) + \#(FP)};$$

calculate precision of the initial model: and $$Pre = \frac{\#(TP)}{\#(TP) + \#(FP)};$$

calculate accuracy of the initial model:

$$Acc = \frac{\#(TP) + \#(TN)}{\#(TP + TN + FN + FP)};$$

where TP represents a correctly recognized atrial fibrillation signal, FP represents an incorrectly recognized atrial fibrillation signal, TN represents a correctly recognized normal signal, and FN represents an incorrectly recognized normal signal; determine whether the sensitivity, the specificity, the precision, and the accuracy meet corresponding thresholds respectively; if no, adjust configuration parameters in the network structure until the sensitivity, the specificity, the precision, and the accuracy meet the corresponding thresholds; and determine the initial model as the atrial fibrillation signal recognition model.

According to the atrial fibrillation signal recognition apparatus provided in this embodiment of the present disclosure, multiple convolutional neural networks with different sizes of receptive fields are used to recognize atrial fibrillation signals, so that atrial fibrillation signals of different granularities can be recognized. This can comprehensively recognize atrial fibrillation signals, thereby improving the reliability and accuracy of atrial fibrillation signal recognition. In addition, this method requires short duration of the electrocardiogram signal, and no manual intervention is required in the recognition process, so that atrial fibrillation signals can be automatically and efficiently recognized.

Figure 7:
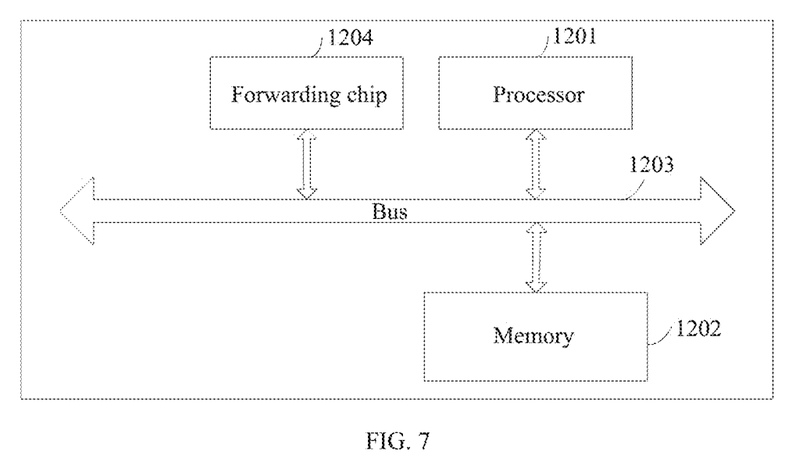
FIG. 7 is a schematic structural diagram of an atrial fibrillation signal recognition device according to an embodiment of the present disclosure.

An embodiment provides an atrial fibrillation signal recognition device corresponding to the foregoing method embodiment. FIG. 7 is a schematic structural diagram of the recognition device. As shown in FIG. 7, the device includes a processor 1201 and a memory 1202. The memory 1202 is configured to store one or more computer instructions. The one or more computer instructions are executed by the processor to perform the foregoing atrial fibrillation signal recognition method.

The recognition device shown in FIG. 7 further includes a bus 1203 and a forwarding chip 1204. The processor 1201, the forwarding chip 1204, and the memory 1202 are connected by using the bus 1203. The recognition device may be a network edge device.

The memory 1202 may include a high speed random access memory (RAM), or may further include a non-volatile memory, for example, at least one magnetic disk memory. The bus 1203 may be an ISA bus, a PCI bus, an EISA bus, or the like. The bus can be classified into an address bus, a data bus, a control bus, etc. For ease of representation, the bus is represented by using only one double-headed arrow in FIG. 7. However, it does not mean that there is only one bus or only one type of bus.

The forwarding chip 1204 is configured to connect to at least one user terminal and other network elements through a network interface, and send an encapsulated IPv4 packet or IPv6 packet to the user terminal through the network interface.

The processor 1201 may be an integrated circuit chip and has a signal processing capability. During implementation, the steps of the foregoing method can be implemented by using a hardware integrated logic circuit in the processor 1201, or by using instructions in a form of software. The processor 1201 may be a general-purpose processor, including a central processing unit (CPU), a network processor (NP), and the like; or may also be a digital signal processor (DSP), an application-specific integrated circuit (ASIC), a field programmable gate array (FPGA), or another programmable logic device, a discrete gate, a transistor logic device, or a discrete hardware component. All methods, steps, and logical block diagrams disclosed in the embodiments of the present disclosure can be implemented or performed. The general-purpose processor may be a microprocessor or the processor may be any conventional processor, etc. Steps of the methods disclosed with reference to the embodiments of the present disclosure may be directly performed and accomplished through a hardware decoding processor, or may be performed and accomplished by using a combination of hardware and software modules in the decoding processor. The software module may be located in a mature storage medium in the art, such as a random access memory, a flash memory, a read-only memory, a programmable read-only memory, an electrically erasable programmable memory, or a register. The storage medium is located in the memory 1202, and the processor 1201 reads information in the memory 1202 and completes the steps of the methods in the foregoing embodiments in combination with hardware of the processor 1201.

An embodiment of the present disclosure further provides a machine-readable storage medium, where the machine-readable storage medium stores a machine-executable instruction; and when being invoked and executed by a processor, the machine-executable instruction enables the processor to perform the foregoing atrial fibrillation signal recognition method. For specific implementation, refer to the method embodiments. Details are not described herein again.

According to the atrial fibrillation signal recognition method, apparatus and device provided in the embodiments of the present disclosure, no artificial feature engineering is required, and a function of automatically extracting electrocardiogram features is provided; two VGG-16 networks are used, but the two networks have convolution kernels of different granularities, thereby capturing more feature information of different granularities.

In the several embodiments provided in this application, it should be understood that the disclosed apparatus and method may be implemented in other manners. The apparatus embodiments described above are merely examples. For example, the flowcharts and block diagrams in the accompanying drawings show the architectures, functions, and operations that may be implemented according to the apparatuses, methods, and computer program products in multiple embodiments of the present disclosure. In this regard, each block in the flowchart or block diagram may represent one module, one program segment, or one part of code. The module, the program segment, or the part of code includes one or more executable instructions for implementing specified logical functions. It should also be noted that, in some alternative implementations, the functions marked in the blocks may occur in an order different from that marked in the figures. For example, two consecutive blocks can actually be executed in parallel, and sometimes they can also be executed in reverse order, depending on the function involved. It should also be noted that, each block in the block diagram and/or flowchart, and a combination of blocks in the block diagram and/or flowchart can be implemented by using a dedicated hardware-based system that performs a specified function or action, or can be implemented by using a combination of dedicated hardware and computer instructions.

In addition, functional modules in the embodiments of the present disclosure may be integrated into one independent part, or each of the modules may exist alone, or two or more modules may be integrated into one independent part.

When the functions are implemented in the form of a software functional unit and sold or used as an independent product, the functions may be stored in a computer-readable storage medium. Based on such an understanding, the technical solutions in the present disclosure essentially, or the part contributing to the prior art, or some of the technical solutions may be implemented in a form of a software product. The computer software product is stored in a storage medium and includes several instructions for instructing a computer device (which may be a personal computer, a server, a network device, or the like) to perform all or some of the steps of the methods described in the embodiments of the present disclosure. The foregoing storage medium includes: any medium that can store program code, such as a USB flash drive, a removable hard disk, a read-only memory (ROM), a random access memory (RAM), a magnetic disk, or an optical disc.

Finally, it should be noted that the foregoing embodiments are merely specific implementations of the present disclosure, and are intended for describing the technical solutions in the present disclosure but not for limiting the present disclosure. The protection scope of the present disclosure is not limited thereto. Although the present disclosure is described in detail with reference to the foregoing embodiments, persons of ordinary skill in the art should understand that they may still make modifications to the technical solutions described in the foregoing embodiments, or readily figure out variations, or make equivalent replacements to some technical features thereof, within the technical scope disclosed in the present disclosure. However, these modifications, variations, or replacements do not make the essence of the corresponding technical solutions depart from the spirit and scope of the technical solutions in the embodiments of the present disclosure, and therefore shall fall within the protection scope of the present disclosure. Therefore, the protection scope of the present disclosure shall be subject to the protection scope of the appended claims.

What is claimed is:

1. An atrial fibrillation signal recognition method, wherein the method comprises:
   obtaining an electrocardiogram signal to be recognized; and
   inputting the electrocardiogram signal to be recognized to a pre-established atrial fibrillation signal recognition model, and outputting an atrial fibrillation signal recognition result, wherein
   the atrial fibrillation signal recognition model is established in the following way:
   obtaining a specified number of electrocardiogram sample signals and corresponding identifier information, wherein the identifier information comprises identifier information of normal signals and of atrial fibrillation signals;
   balancing, according to the number of normal signals, the atrial fibrillation signals by means of synthetic minority oversampling technique (SMOTE);
   establishing a network structure of multiple convolutional neural networks, each of the convolutional neural networks being provided with a specific receptive field for recognizing the atrial fibrillation signals of a corresponding granularity; and
   inputting the normal signals and the balanced atrial fibrillation signals to the network structure for training, to generate the atrial fibrillation signal recognition model;
   wherein the network structure of multiple convolutional neural networks comprises a first network and a second network;
   both the first network and the second network are VGG-16 convolutional neural networks; each of the first network and the second network comprises multiple convolutional lavers and multiple max-pooling layers; a receptive field of a convolution kernel in the first network is less than or equal to a receptive field of a convolution kernel in the second network;
   max-pooling lavers of the last layers of the first network and the second network are connected to each other; the interconnected max-pooling layers are further successively connected to multiple fully connected layers and a Softmax layer.

2. The method according to claim 1, wherein the step of obtaining an electrocardiogram signal to be recognized comprises:
   obtaining an original electrocardiogram signal; and
   preprocessing the original electrocardiogram signal to generate an electrocardiogram signal to be recognized, wherein the preprocessing comprises filtering processing and regularization processing.

3. The method according to claim 1, wherein the step of inputting the normal signals and the balanced atrial fibrillation signals to the network structure for training, to generate the atrial fibrillation signal recognition model comprises:
  inputting the normal signals and the balanced atrial fibrillation signals to the network structure for training, to generate an initial model;
  calculating sensitivity of the initial model:

$$Sen = \frac{\#(TP)}{\#(TP) + \#(FN)};$$

calculating specificity of the initial model:

$$Spe = \frac{\#(TN)}{\#(TN) + \#(FP)};$$

calculating precision of the initial model:

$$Pre = \frac{\#(TP)}{\#(TP) + \#(FP)};$$

calculating accuracy of the initial model:

$$Acc = \frac{\#(TP) + \#(TN)}{\#(TP + TN + FN + FP)};$$

wherein IP represents a correctly recognized atrial fibrillation signal; FP represents an incorrectly recognized atrial fibrillation signal; TN represents a correctly recognized normal signal;
FN represents an incorrectly recognized normal signal;
  determining whether the sensitivity, the specificity, the precision, and the accuracy meet corresponding thresholds respectively; if no, adjusting configuration parameters in the network structure until the sensitivity, the specificity, the precision, and the accuracy meet the corresponding thresholds; and
  determining the initial model as the atrial fibrillation signal recognition model.

4. An atrial fibrillation signal recognition device, comprising a processor and a non-transitory ma.chine-readable storage medium, wherein the non-transitory machine-readable storage medium stores a machine-executable instruction that is executable by the processor, and the processor is configured to execute the machine-executable instruction to perform the method according to claim 1.

5. An atrial fibrillation signal recognition device, comprising a processor and a non-transitory machine-readable storage medium, wherein the non-transitory machine-readable storage medium stores a machine-executable instruction that is executable by the processor, and the processor is configured to execute the machine-executable instruction to perform the method according to claim 2.

6. An atrial fibrillation signal recognition device, comprising a processor and a non-transitory machine-readable storage medium, wherein the non-transitory machine-readable storage medium stores a machine-executable instruction that is executable by the processor, and the processor is configured to execute the machine-executable instruction to perform the method according to claim 3.

7. A non-transitory machine-readable storage medium, wherein non-transitory the machine-readable storage medium stores a machine-executable instruction, and when the machine-executable instruction is invoked and executed by a processor, the machine-executable instruction enables the processor to perform the method according to claim 1.

8. A non-transitory machine-readable storage medium, wherein the non-transitory machine-readable storage medium stores a machine-executable instruction, and when the machine-executable instruction is invoked and executed by a processor, the machine-executable instruction enables the processor to perform the method according to claim 2.

9. A non-transitory machine-readable storage medium, wherein the non-transitory machine-readable storage medium stores a machine-executable instruction, and when the machine-executable instruction is invoked and executed by a processor, the machine-executable instruction enables the processor to perform the method according to claim 3.

* * * * *